US012741055B2

(12) United States Patent
Zhang et al.

(10) Patent No.: US 12,741,055 B2
(45) Date of Patent: Sep. 22, 2026

(54) POLYSACCHARIDE-BASED HYDROGEL SCAFFOLDS FOR WOUND CARE

(71) Applicants: ROQUETTE FRERES, Lestrem (FR); NATIONAL UNIVERSITY OF SINGAPORE, Singapore (SG)

(72) Inventors: Chi Zhang, Singapore (SG); Shiqi Hong, Singapore (SG); Rajeev Gokhale, Singapore (SG); Pui Lai Rachel Ee, Singapore (SG); Jian Yao Ng, Singapore (SG)

(73) Assignees: Roquette Freres, Lestrem (FR); National University of Singapore, Singapore (SG)

( * ) Notice: Subject to any disclaimer, the term of this patent is extended or adjusted under 35 U.S.C. 154(b) by 1003 days.

(21) Appl. No.: 17/594,935

(22) PCT Filed: May 7, 2020

(86) PCT No.: PCT/EP2020/062647

§ 371 (c)(1), (2) Date: Nov. 3, 2021

(87) PCT Pub. No.: WO2020/225336

PCT Pub. Date: Nov. 12, 2020

(65) Prior Publication Data

US 2022/0218868 A1 Jul. 14, 2022

(30) Foreign Application Priority Data

May 7, 2019 (EP) .................................... 19305581

(51) Int. Cl.

*A61L 26/00* (2006.01)
*C12N 1/12* (2026.01)

(52) U.S. Cl.

CPC ......... *A61L 26/008* (2013.01); *A61L 26/0052* (2013.01); *C12N 1/12* (2013.01); *A61L 2300/802* (2013.01)

(58) Field of Classification Search

CPC ............... A61L 26/008; A61L 26/0023; A61L 26/0047; A61L 26/0052; A61L 26/0066;
(Continued)

(56) References Cited

U.S. PATENT DOCUMENTS 5,945,100 A * 8/1999 Fick ........................ A61P 35/00 424/428
8,114,292 B2 2/2012 Da Costa
(Continued)

FOREIGN PATENT DOCUMENTS

CN 101590293 A 12/2009
CN 102532566 A 7/2012
(Continued)

OTHER PUBLICATIONS

Huan Cao, et al., "Mechanoregulation of Cancer-Associated Fibroblast Phenotype in Three-Dimensional Interpenetrating Hydrogel Networks", Langmuir, vol. 35, No. 23, Nov. 27, 2018 (Nov. 27, 2018), pp. 7487-7495, XP055716062; p. 7488, right-hand column, paragraph 2 figure 1 p. 7489, right-hand column, paragraph 3—p. 7490, left-hand column, paragraph 1.
(Continued)

*Primary Examiner* — Hong Yu

(57) ABSTRACT

The present invention relates to a hydrogel comprising polysaccharide polymer network and collagen, particularly for use in the wound treatment. The present invention also relates to a wound dressing and a cell culture system comprising the hydrogel and their use in the wound treatment.

15 Claims, 11 Drawing Sheets

(58) Field of Classification Search
CPC .. A61L 26/0095; A61L 2300/802; C08L 1/26; C08L 5/02; C08L 5/04; C08L 5/06; C08L 5/08; C08L 5/12; C08L 89/06; C12N 1/12
See application file for complete search history.

(56) References Cited

U.S. PATENT DOCUMENTS

| | | | | |
|---|---|---|---|---|
| 2005/0054595 | A1 * | 3/2005 | Binette | A61P 5/00 514/44 R |
| 2008/0124318 | A1 * | 5/2008 | Lisson | A61P 39/00 424/93.4 |
| 2015/0005395 | A1 | 1/2015 | Chung et al. | |
| 2016/0325017 | A1 * | 11/2016 | Pereira Da Silva | C08J 3/075 |
| 2016/0367358 | A1 | 12/2016 | Tran | |
| 2017/0182209 | A1 * | 6/2017 | Branco da Cunha | A61L 26/0052 |
| 2021/0008124 | A1 * | 1/2021 | Peng | A61P 37/04 |

FOREIGN PATENT DOCUMENTS

| | | | |
|---|---|---|---|
| CN | 102688525 | B * | 11/2013 |
| CN | 104004231 | A | 8/2014 |
| WO | 2014/167513 | A1 | 10/2014 |
| WO | 2015/192017 | A1 | 12/2015 |
| WO | 2017/013414 | A1 | 1/2017 |

OTHER PUBLICATIONS

Database WPI Week 201431, Thomson Scientific, London, GB; AN 2014-E08957 XP002795411, & CN 103 484 429 A (Qingdao Maidisaisi Biological Technology) Jan. 1, 2014 (Jan. 1, 2014), abstract.

Database WPI Week 201856 Thomson Scientific, London, GB; AN 2018-593623 XP002795412, & CN 108 309 840 A (Guangzhou Liyanzhuang Biology Technology) Jul. 24, 2018 (Jul. 24, 2018) abstract, -& Database CA [Online] Chemical Abstracts Service, Columbus, Ohio, US; XP002795413, retrieved from STN Database accession No. 169:247937.

The International Search Report and Written Opinion, mailed on Jul. 28, 2020, in the corresponding PCT Appl. No. PCT/EP2020/062647.

The Australian Examination Report No. 1, issued on May 9, 2025, in the related Australian Appl. No. 2020267858.

* cited by examiner

POLYSACCHARIDE-BASED HYDROGEL SCAFFOLDS FOR WOUND CARE

FIELD OF THE INVENTION

The present invention relates to a hydrogel comprising polysaccharide polymer network and collagen, particularly for use in the wound treatment. The present invention also relates to a wound dressing and a cell culture system comprising the hydrogel and their use in the wound treatment.

BACKGROUND OF THE INVENTION

The human body is able to restore skin integrity after injury with a minimal scar via a complex process involving coagulation and hemostasis, inflammation, proliferation and remodeling. However, the healing process could be interrupted by local or systemic factors, and medical treatment could be required.

Therefore, a wide range of wound care products have been developed to improve the life quality of those who suffer from wounds. Wound dressing provides an optimal microenvironment to the wound or by delivering bioactive molecules to accelerate wound healing.

The current state-of-the-art in wound care products reflects a move from simple dressings (i.e. bandages) to active products and devices that incorporate pharmaceutically active ingredients. Proven to perform key roles such as conferring a moist environment for healing, minimizing the risk of infections, and removing excess unwanted fluids. What is evident from the range of advanced products is the predominance of hydrogel dressings. The high water content of the gel is particularly compatible with the exposed surface of the wound and healing is significantly enhanced. By using a gel comprising a relatively high concentration of hydrophilic polymer material, the gel can function particularly effectively to take up water e.g. wound exudate in use of the dressing while in contact with a wound. Because the gel is an aqueous system, use of the dressing does not have the effect of inducing an overall dryness of the wound which would be undesirable.

Hydrogels are made up of physically or chemically crosslinked polymers derived from natural or synthetic sources. A large proportion of these hydrogels is synthetic in origin with limited cell compatibility and biodegradability. The other huge gap exists in the reliance on animal-derived materials for supporting cell growth which continue to pose problems such as immunogenicity and risk of infection.

Plant-polysaccharide polymers such as gellan gum have been used for fabricating hydrogel. Gellan gum hydrogels are biocompatible and exhibit good mechanical properties for tissue engineering. For instance, Cencetti et al. developed a hydrogel composed of gellan gum and sulphated hyaluronan which acts as structural and anti-adhesive component (Cencetti et al. 2011; J. Mater. Sci.; 22:263-271). Cerqueira et al. described a hyaluronic acid/gellan gum spongy-like hydrogel for use in the wound treatment with cell adhesion. However, the data was shown for cells cultures up to only two days (WO2014/167513; Cerqueira et al. 2014, ACS Appl. Mater. Interfaces; 6:19668-19679).

Shin et al. developed a double network hydrogels by using a two-step photo-crosslinking of two modified biomacromolecules, gellan gum methacrylate and gelatin methacrylamide which is cell-compatible (Shin et al. 2012; biomaterials; 33(11):3143-3152). In this study, cell viability was only showed for few days. Mat Amin et al. incorporate TiO2 particles in gellan gum hydrogel to improve cell adhesion. However TiO2 nanoparticles incorporation only improves an initial attachment of cells on hydrogel and does not allow a long-term cell growth (Mat Amin et al. 2012; Macromolecular bioscience; 12:374-82).

Thus, it remains a need to develop more effective solution with biocompatible polysaccharide hydrogel comprising attachment sites for cells anchorage allowing long-term cell growth.

SUMMARY OF THE INVENTION

The inventors developed a new polysaccharide polymer hydrogel consisting of an interpenetrating polymer network (IPN) of gellan gum with collagen to form interpenetrating hydrogels. The presence of collagen at low concentration remarkably improved the long-term survival of cells. Moreover, the inventors also showed that an algae growth factor such as *chlorella* grow factor improves cell viability of encapsulated cells within the gellan gum hydrogels.

Thus, the invention relates to a hydrogel comprising a polysaccharide polymer network and collagen, preferably an interpenetrating polymer network comprising crosslinked polysaccharide polymer and collagen for use in the wound treatment in a subject in need thereof. In a preferred embodiment, said hydrogel comprises less than 0.2% (w/v) of collagen In another preferred embodiment, said polysaccharide polymer is gellan gum. The hydrogel for use according to the invention preferably comprises from 0.1% (w/v) to 10% (w/v) of gellan gum. In another preferred embodiment, the gellan gum of hydrogel is cross-linked by Mg2+. The hydrogel for use according to the invention can also further comprise an algae growth factor, preferably *chlorella* growth factor, more preferably between 0.1 and 1% (w/v) of *chlorella* growth factor.

The present invention also relates to a wound dressing comprising the hydrogel according to the invention, and preferably an algae growth factor, more preferably *chlorella* growth factor. Said wound dressing can further comprise a pharmaceutically acceptable carrier. The present invention also relates to a wound dressing for use in the wound treatment in a subject in need thereof.

In another aspect, the invention relates to a hydrogel comprising a polysaccharide polymer network and collagen and algae growth factor, preferably *chlorella* growth factor.

Finally, the present invention relates to a cell culture system comprising a hydrogel as described above and a cell culture medium comprising an algae growth factor, preferably said cell culture medium is free of serum or albumin.

FIG. 3. A) Validity of cell-adhesive 3D microenvironment of IPN hydrogels. Behavior of ADSC encapsulated within IPN hydrogel was studied with CLSM. F-actin (cytoskeleton) of cells were stained with Phalloidin-iFluor 488 Reagent and z-stack images of encapsulated ADSC were captured to analyze the entirety of the IPN hydrogels' 3D network. ADSC were homogeneously distributed throughout the hydrogels. Filopodia were observed from day 1, and ADSC continues to proliferate and spread over 21 days of incubation. Cell-laden IPN hydrogels were fabricated within 4-well chamber glass slides. All samples were incubated at 37° C. in a humidified atmosphere with 5% $CO_2$, and the media were changed every 2-3 days (Mon, Wed and Fri). Scale bar: 100 μm. B) Validity of cell-adhesive 3D microenvironment of pure gellan gum hydrogels. Behavior of encapsulated hMSC were observed. F-actin (cytoskeleton) of cells were stained with Phalloidin-iFluor 488 Reagent and z-stack images were captured with CLSM to analyze the entirety of cell-laden pure gellan gum hydrogels. Cells were seen to be homogeneously distributed throughout the hydrogels immediately after seeding. Filopodia were observed from day 1, and cells continue to proliferate and spread over full duration of incubation. All samples were incubated at 37° C. in a humidified atmosphere with 5% $CO_2$, and the media were changed every 2-3 days (Mon, Wed and Fri). Scale bar: 100 μm.

Figure 4:
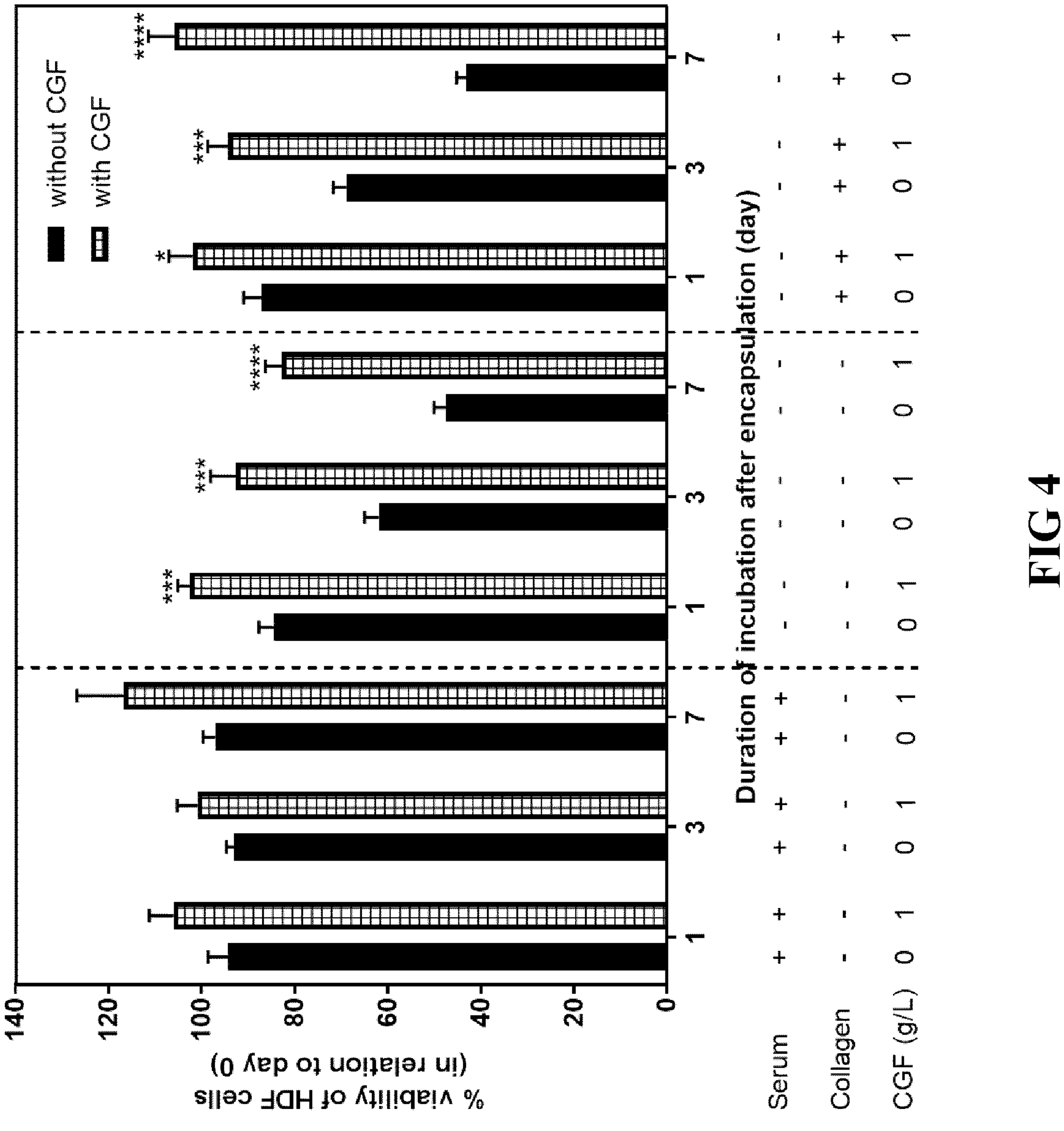

FIG. 4: Cell viability of encapsulated HDF in pure gellan gum or IPN hydrogels in contact with cell culture media supplemented with or without CGF. Cells were seeded in 96-well plates at a density of $1\times10^6$ cells/mL of hydrogel. Cell viability was expressed in percentage in relation to day 0. The mean (n=3) and standard error of mean (SEM) are shown. All samples were incubated at 37° C. in a humidified atmosphere with 5% $CO_2$, and the media were changed every 2-3 days (Mon, Wed and Fri).

Figure 5:
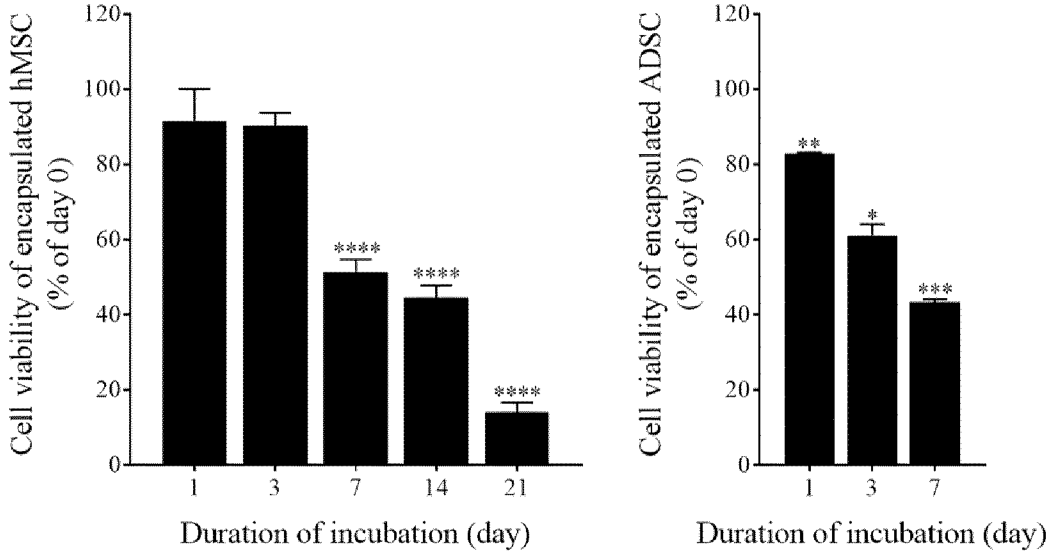

FIG. 5: Cell environment of pure gellan gum hydrogels. Cell viability of encapsulated A) hMSC and B) ADSC (*$p<0.05$, $p<0.005$, *$p<0.0005$, ****$p<0.0001$). The mean (n=3) and SD are shown.

Figure 6:
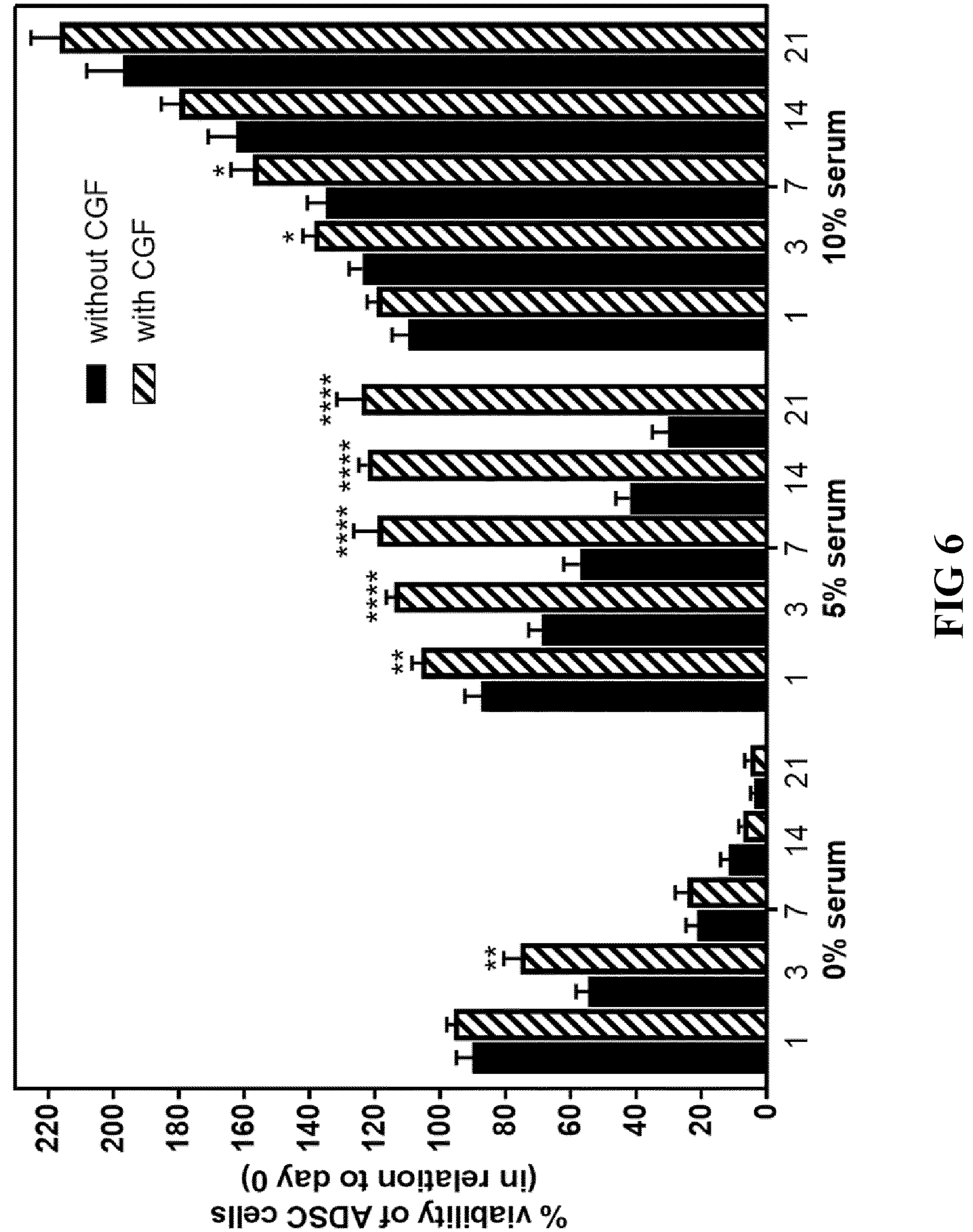

FIG. 6: Cell viability of ADSC encapsulated within gellan gum-collagen IPN hydrogels, incubated in culture media supplemented with various concentrations of FBS and CGF. Cells were seeded in 48-well plates at a density of $1\times10^6$ cells/mL of hydrogel. The viability of ADSC was measured using CellTiter 96® AQueous One Solution Cell Proliferation Assay (MTS) on day 0, 1, 3, 7, 14 and 21. Cell proliferation was determined by expressing the viability on day 1, 3, 7, 14 and 21 in relation to day 0. The mean (n=3) and standard error of mean (SEM) are shown. All samples were incubated at 37° C. in a humidified atmosphere with 5% $CO_2$, and the media were changed every 2-3 days (Mon, Wed and Fri).

FIG. 7: Evaluation of the wound healing potential of ADSC-laden IPN hydrogel via in vitro scratch assay. A) Representative images of migration of HDF over a period of 48 hour into a wounded area created by the presence of a mechanical insert producing a 0.9 mm cell-free distance. The HDF was exposed to either normal media, ADSC-equilibrated, gel-equilibrated or serum-free media. ADSC-equilibrated media was collected after culturing serum-free media with ADSC-laden hydrogel for 72 hour while gel-equilibrated media was collected after culturing serum-free media with cell-free hydrogel for 72 hour. Non-equilibrated culture media with FBS was used as positive controls (normal) and non-equilibrated culture media without FBS was used as negative controls (serum-free). All culture media contains 10 ng/mL of TNF-α. B) Migration of HDF exposed to ADSC-equilibrated media was not statistically significantly different to migration of HDF exposed to normal media (*$p<0.05$, $p<0.005$, *$p<0.0005$, ****$p<0.0001$). However, the migration of HDF exposed to ADSC-equilibrated media was statistically significantly different from HDF exposed to gel-equilibrated media. The mean (n=3) and standard error of mean (SEM) are shown. All samples were incubated at 37° C. in a humidified atmosphere with 5% $CO_2$.

Figure 8:
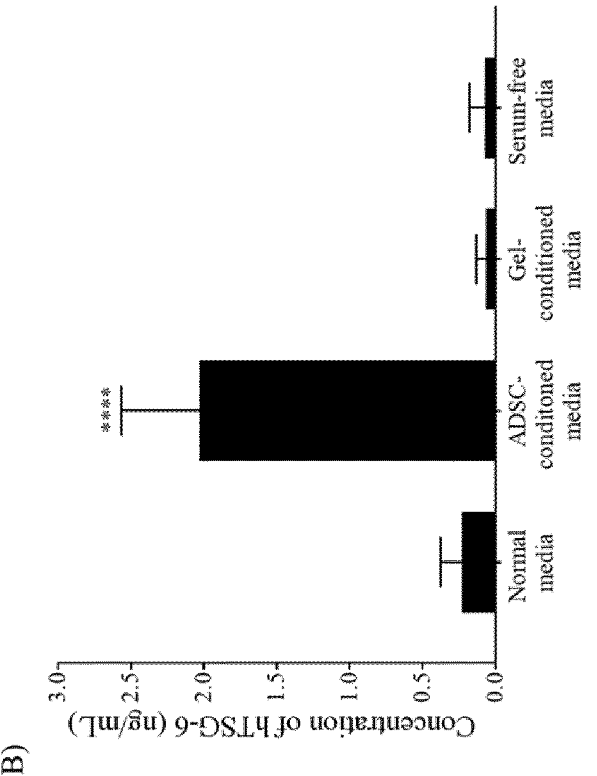
Figure 8:
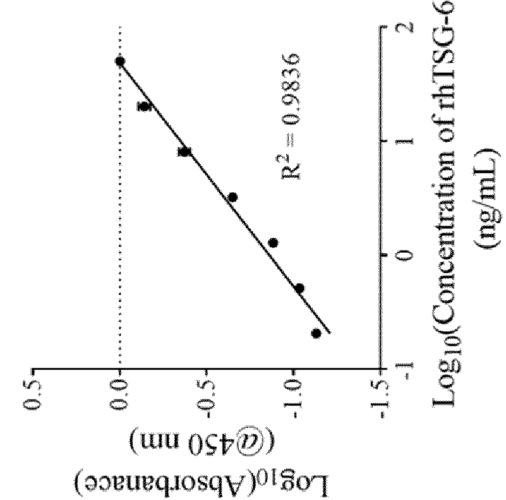

FIG. 8: ELISA assay for human TSG-6. A) Calibration curve of human TSG-6 ELISA. $\text{Log}_{10}(\text{Absorbance})=0.5104*\text{Log}_{10}[\text{human TSG-6}]\text{ng/mL}-0.8578$. The unknown human TSG-6 concentrations can be calculated from the formula: [TSG-6]ng/mL=10^([log $(abs_{450})$+0.8578]/0.5104). B) Concentration of human TSG-6 detected in normal, ADSC-conditioned, gel-conditioned and serum-free media. Values were calculated from calibration curve. ADSC-equilibrated media was found to contain a statistically significantly higher amount of human TSG-6 (*$p<0.05$, $p<0.005$, *$p<0.0005$, ****$p<0.0001$) than other forms of culture media. The mean (n=5) and SD are shown.

Figure 9:
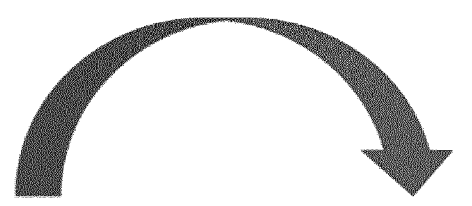
Figure 9:
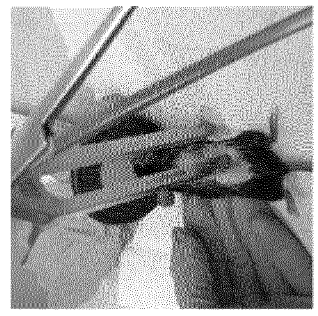
Figure 9:
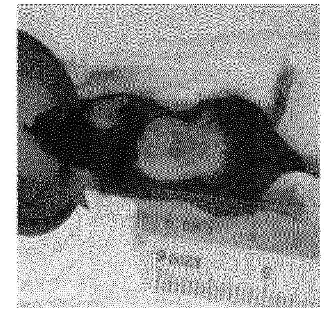
Figure 9:
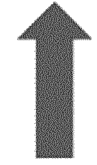
Figure 9:
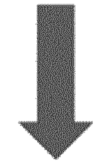
Figure 9:
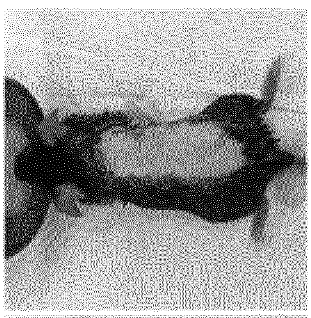
Figure 9:
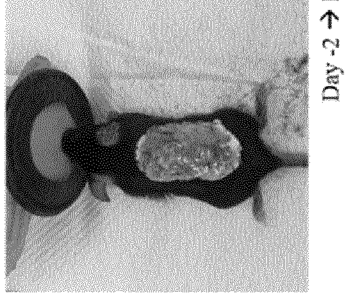
Figure 9:

FIG. 9: In vivo full-thickness burn wound creation procedure.

DETAILED DESCRIPTION OF THE INVENTION

The inventors developed a new hydrogel comprising a polysaccharide polymer network and collagen allowing long-term cell survival. Thus, the present invention relates to a hydrogel comprising a polysaccharide polymer network and collagen.

The term "hydrogel" as used herein refers to hydrophilic macromolecular networks which are produced by chemical or physical crosslinking of soluble polymers that confer the hydrogels the capability to absorb and retain a high content of water, acquiring a visco-elastic character and facilitating the transport of oxygen, nutrients and waste.

According to the invention, the hydrogel comprises a polysaccharide polymer network. As used herein, the term "polysaccharide" refers to polysaccharides and their derivatives.

Polysaccharides refer to polymeric carbohydrate structures formed of repeating units joined together by glucosidic bonds. These structures can be linear and can contain various degrees of branching. The term "polysaccharide" refers to a single polysaccharide or a mixture of two or more polysaccharides. In a preferred embodiment, said polysaccharide is a single polysaccharide. In accordance with the present invention the polysaccharide is preferably selected from the group consisting of polysaccharide of animal origin, polysaccharide of plant origin, polysaccharide of algal origin, polysaccharide of bacterial origin; and any mixture thereof, preferably polysaccharide of plant origin. More preferably, the polysaccharide is selected from the group consisting of xanthan gum, gellan gum, λ-carrageenan and κ-carrageenan, ι-carrageenan, alginates, pectins, carboxymethylcellulose, agar-agar, arabic gum, hyaluronates, dextran and any mixture thereof, preferably from gellan gum, xanthan gum, carrageenan, guar gum and dextran.

In a preferred embodiment, said polysaccharide is a gellan gum. Gellan gum is a polysaccharide secreted by *Sphingomonas paucimobilis* that was initially described by Moorhouse R. et al. 1981. ACS symposium Series. No. 150, p. 111. It consists of tetrasaccharide repeat units containing β-D-glucose, β-D-glucuronic acid and α(L-rhamnose monomers in the molar ratio 2:1:1. It exists commonly in two formulations: one with a high acyl content which is the raw product secreted by the bacteria, and another with low acyl content due to processing, which is the wider known. Gellan gum includes, but is not limited to, low-acyl gellan gum, high-acyl gellan gum, chemically modified gellan gum, or any mixture of these gellan gum polymers. Preferably, said gellan gum is a low-acyl gellan gum.

The polysaccharide hydrogel may be obtained by mixing the polysaccharide with a crosslinking agent. In a preferred embodiment, when the polysaccharide is a gellan gum, the ionic cross-linking agent is a cation, more preferably a divalent cation. Said divalent cation can be selected from the group consisting of: Ca2+, Mg2+, Mn2+, Cu2+, Sr2+, Zn2+, Ra2+, Be2+, preferably Mg2+. The concentration of said divalent cation, preferably Mg2+ is between 0.01% (w/v) and 0.03% (w/v), more preferably is 0.02% (w/v).

In an embodiment for better results, the concentration of the polysaccharide in the hydrogel preferably gellan gum of the present invention may be between 0.1% and 10% (w/v), preferably 0.2% and 5% (w/v), more preferably 0.2% and 2.5% (w/v), or between 0.2% and 1% (w/v). Even more preferably, the concentration of gellan gum in the hydrogel is 0.4% (w/v).

In particular, polysaccharides such as gellan gum or carrageenan required the presence of ions for the formation of a stable hydrogel. Polysaccharide can be homogeneously dispersed in a solvent at a temperature that promotes the linearization of its chain and may by decreasing the temperature and in the presence of ions form a hydrogel. According to the invention, a suitable solvent is an aqueous solution, preferably water, a cell culture media, an aqueous saline solvent, or mixtures thereof. The water used according to the invention may be purified water or sterilized water.

In addition to the gelation catalyzed by the temperature, it is also possible to form polysaccharide hydrogels by varying the pH of the aqueous solution.

The inventors showed that the hydrogel comprising full interpenetrating network formed by collagen with gellan gum improves the long-term cell survival. Thus, the hydrogel according to the present invention comprises collagen. In a preferred embodiment, said hydrogel comprises a full interpenetrating polymer network comprising crosslinked polysaccharide polymer and crosslinked collagen. The collagen may be selected from native collagens such as types I, II or III native collagens, atelopeptide collagen and regenerated collagen. In a preferred embodiment, the collagen is type I collagen. In a preferred embodiment, the hydrogel comprises less than 0.2% (w/v), preferably between 0.2 and 0.1% (w/v) of collagen, more preferably 0.1% of collagen. Preferably the hydrogel comprises less than 0.20% of type I collagen, more preferably between 0.2 and 0.1%, more preferably 0.1% of type I collagen.

The hydrogel may additionally comprise one or more active therapeutic or antimicrobial agents. Suitable therapeutic agents include growth factors, analgesics, local anaesthetics and steroids. Suitable antimicrobial agents include antiseptics such as silver compounds (e.g. silver sulfadiazine) and chlorhexidine, and antibiotics.

The inventors showed that the hydrogel of the invention with an algae growth factor particularly improves cell survival. Thus, in a particular embodiment, an algae growth factor is incorporated into the hydrogel of the invention. This can be achieved by treating the hydrogel with an algae growth factor solution or by mixing polysaccharide with a solvent comprising an algae growth factor before gelation.

An algae extract exhibits growth promotion on cells and is referred herein as an algae growth factor. According to the invention, an algae growth factor means any fraction, extract, or isolated or purified molecule from an alga cell. In one embodiment, the component is a protein or nucleic acid. In another embodiment, the component is a phytochemical. In another embodiment, the component is a fraction of algae. Extracts may be prepared according to suitable techniques known in the art, such as for example by alkaline dissolution or organic solvent extraction, high-pressure homogenization, bead milling as described in U.S. Pat. No. 5,330,913. A preferred method used to extract algae, in particular *chlorella* is described in WO2016/009145.

By "algae" it is meant photosynthetic eukaryotic organisms which include organisms ranging from unicellular microalgae genera, such as *chlorella* and the diatoms, to multicellular forms. According to the invention, the alga is preferably a green alga, more preferably from chlorophyta phylum. In a preferred embodiment, said alga is a *chlorella* which refers to a genus of a unicellular green alga. *Chlorella* species include but are not limited to *chlorella acuminate, chlorella antartica, chlorella bacteroidea, chlorella botryoides, chlorella chlorelloides, chlorella colonialis, chlorella conglomerate, chlorella elongata, chorella faginea, chlorella gloriosa, chlorella heliozoae, chlorella infusionum, chlorella ewinii, chlorella marina, chlorella miniata, chlorella nocturna, chlorella nordstedti, chlorella pyrenoidosa, Chlorella vulgaris* and *chlorella sorokiniana*, preferably *chlorella sorokiniana, Chlorella vulgaris* or *chlorella protothecoides*. Many *chlorella* species known can be found in the database AlgaeBase (Guiry, M. D. & Guiry, G. M. 2019. AlgaeBase. World-wide electronic publication, National University of Ireland, Galway. http://www.algaebase.org).

In a preferred embodiment, the *chlorella* growth factor is a fraction or an extract from a *chlorella*, preferably from *chlorella sorokiniana, Chlorella vulgaris* or *chlorella protothecoides*, more preferably *Chlorella vulgaris*.

In a preferred embodiment, the hydrogel according to the invention comprises between 0.05 and 10%, or 0.05 and 5% of *chlorella* growth factor, preferably between 0.1 and 2% (w/v), more preferably between 0.33 and 1% (w/v).

The hydrogel of the invention presents good mechanical properties, in particular in terms of elastic character and stored energy. In particular, the storage modulus (G') of the hydrogel measured at 1 Hz at 25° C. is comprised between 100 to 5000 Pa, preferably between 500 and 5000 Pa, 1000 and 3000 Pa or 2000 and 3000 Pa, more preferably between 2000 and 2500 Pa. The storage modulus (G') according to the invention is measured with an oscillatory rheometer (MCR302, Antor Paar, Austria), using plate-plate geometry (diameter=8 mm, working gap=1 mm) as described in the examples.

Method of Preparing the Hydrogel

The preparation of hydrogel according to the invention comprises the dissolution of polysaccharide in a solvent with collagen and the use of a crosslinking mechanism for reticulation.

In a particular embodiment, the polysaccharide hydrogel is a gellan gum hydrogel and is prepared by thermal and/or ionic cross-linking. In a preferred embodiment, the gellan gum hydrogel of the invention is prepared by dissolving gellan gum in a solvent at a temperature above polymer critical gelling temperature, typically 90° C. and by decreasing the temperature below polymer critical gelling temperature and/or by mixing the gellan gum solution with the ionic cross-linking agent.

In a preferred embodiment, said hydrogel is a full interpenetrating polymer network comprising collagen and polysaccharide polymer, said polysaccharide polymer is crosslinked in the presence of already crosslinked collagen. Thus, collagen can be added after decreasing the temperature below polymer critical gelling temperature and before mixing the gellan gum solution with the ionic cross-linking agent to form an interpenetrating network.

In a preferred embodiment, the gellan gum is heated at 90° C. to uncoil random chains, then cooled at 37° C. to form double helices and ice-cold neutralized collagen is added and mixed into the gellan gum solution before being crosslinked with $MgCl_2$.

In particular, the concentration of the polysaccharide in the hydrogel, preferably gellan gum of the present invention may be between 0.1% and 10% (w/v), preferably 0.2% and 5% (w/v), more preferably between 0.2% and 2.5% (w/v) or 0.2% and 1% (w/v). Even more preferably, the concentration of gellan gum in the hydrogel is 0.4% (w/v).

In a preferred embodiment, the hydrogel comprises less than 0.2% (w/v), preferably between 0.2 and 0.1% (w/v) of collagen, more preferably 0.1% of collagen. Preferably, the hydrogel comprises less than 0.2% of type I collagen, more preferably between 0.2 and 0.1% of type I collagen, more preferably 0.1% of type I collagen.

In a preferred embodiment, the solvent used to prepare the hydrogel is water based solvent, for instance, deionized water, phosphate buffer solution, etc.

In a particular embodiment, the solvent comprises an algae growth factor and the final concentration of the *chlorella* growth factor with respect to the hydrogel is between 0.05 and 10% (w/v) or 0.05 and 5% of *chlorella* growth factor, preferably between 0.1 and 2% (w/v), more preferably between 0.33 and 1% (w/v).

In a preferred embodiment, the ionic crosslinking agent is a cation, preferably a divalent cation, more preferably selected from the group consisting of: Ca2+, Mg2+, Mn2+, Cu2+, Sr2+, Zn2+, Ra2+, Be2+, preferably Mg2+.

Wound Dressing

In another aspect, the invention relates to a wound dressing comprising the hydrogel of the invention. The wound dressing allows the hydrogel of the invention to be placed in contact with the wound. In a particular embodiment, the wound dressing comprises the hydrogel of the invention as an absorbent material and a backing layer. The backing layer provides a barrier to the passage of microorganisms through the dressing. The backing layer can be liquid impermeable or semipermeable. Preferably, the backing layer is permeable to oxygen and water vapour but not permeable to liquid water or wound exudate. The backing layer is also microorganism impermeable. The wound dressing can also comprise an adhesive layer on the backing layer facing the absorbent layer. Preferably, the adhesive layer extends outwardly from the absorbent layer to form an adhesive-coated margin on the backing layer. The adhesive layer and/or backing layer hold the absorbent pad on a wound, and help to maintain a sterile environment around the wound. The adhesive and backing layer are typically thin and flexible.

In a particular embodiment, the wound dressing comprising the hydrogel of the invention may comprise one or more active therapeutic or antimicrobial agents. In a particular embodiment, said active or antimicrobial agents can be added within the hydrogel or added separately in the wound dressing. In a preferred embodiment, the wound dressing further comprises an algae growth factor as described above. Thus, the algae growth factor can be included within the hydrogel or added separately in the wound dressing.

In another particular embodiment, the wound dressing according to the invention may comprise an acceptable topical carrier. The term "acceptable topical carrier" encompasses both pharmaceutically-acceptable carriers and cosmetically-acceptable carriers, and encompasses substantially non-irritating compatible components which are suitable for delivering the active components to the skin. The term "compatible," as used herein, means that the components of the carrier must be capable of being commingled with the hydrogel, in a manner such that there is no interaction which would substantially reduce the efficacy of the hydrogel during use for treating wounds. These carriers must, of course, be of sufficiently high purity and sufficiently low toxicity to render them suitable for chronic topical administration to the skin of humans or lower animals.

Therapeutic Use

Hydrogel or the wound dressing according to the invention may be used for the treatment of wounds in a subject in need thereof.

The term "subject" or "patient" as used herein, refers to mammals. Mammalian species that can benefit from the disclosed methods of treatment include, but are not limited to, humans, non-human primates such as apes, chimpanzees, monkeys, and orangutans, domesticated animals, including dogs and cats, as well as livestock such as horses, cattle, pigs, sheep, and goats, or other mammalian species including, without limitation, mice, rats, guinea pigs, rabbits, hamsters, and the like.

The term "wound" is used to refer broadly to injuries to the skin and mucous membrane. In particular the term "wound" refers to a damaged area of the body, such as a cut, hole and burn in the skin or the flesh. The wound can be a chronic or an acute wound. An acute wound is an injury to the skin, mucous membrane that occurs suddenly due to accident or surgical injury. A chronic wound is a wound that does not heal in an orderly and timely manner. Chronic wounds include but are not limited to venous and arterial ulcers, diabetic ulcers, pressure ulcers, radiation poisoning, infection or ischemia.

As used herein, the term "treatment", "treat" or "treating" refers to any act intended to ameliorate the status of patients. In certain embodiments, such term refers to the amelioration of the wound healing. As used here the term "wound healing" refers to an intricate process in which the skin or mucous membrane repairs itself after injury.

In a related aspect, the invention pertains to the use of the hydrogel or the wound dressing of the invention in the preparation of a medicament for use in the treatment of a wound.

In a further aspect, the present invention relates to a method of treating wound in a subject in need thereof that comprises administering topically a therapeutically efficient amount of a hydrogel or a wound dressing according to the invention to the surface of a wound of a subject. Topical administration includes application onto the skin and mucous membranes.

This topical administration can be as a single dose or as repeated doses given at multiple designated intervals. It will readily be appreciated by those skilled in the art that the preferred dosage regimen will vary with the type and severity of the injury being treated.

By "therapeutically effective amount" refers to an amount effective, at dosages and for periods of time necessary to achieve the desired therapeutic result such as accelerated wound healing. The therapeutically effective amount of the hydrogel or the wound dressing that comprises it may vary according to factors such as the wound type (mechanical or thermal, full or partial thickness, etc.), the size of the wound, the wound's depth (if full thickness), the absence or presence of infection, time elapsed since the injury's infliction, and the age, physical condition, existence of other disease states, and nutritional status of the patient.

Dosage regimens may be adjusted to provide the optimum therapeutic response. A therapeutically effective amount is also typically one in which any toxic or detrimental effect of the product or pharmaceutical composition is outweighed by the therapeutically beneficial effects.

Cell Culture System

The hydrogel of the invention is suitable for culturing and supporting cells. Therefore, the present invention also relates to a cell culture system comprising the hydrogel of the invention and a culture medium comprising an algae growth factor. In particular, the cell culture system comprises a hydrogel comprising a polysaccharide polymer network and collagen and a culture medium comprising an algae growth factor.

In particular, the culture cell system may be a 2D or 3D culture cell system. In 2D culture cell system, the cells are cultured on the hydrogel of the invention in cell culture medium. In 3D culture system, the cells are embedded within the hydrogel of the invention in a cell culture medium.

The culture cell medium can comprise a basal medium comprising at least one or more components which allows culturing and supporting cells. Numerous basal media are available commercially and are well-known to the person skilled in the art. This medium may be a minimum medium particularly comprising mineral salts, amino acids, vitamins and a carbon source essential to cells and a buffer system for regulating pH. The basal medium able to be used in the method according to the invention includes, for example, but are not limited to, DMEM/F12 medium, DMEM medium, RPMI medium, Ham's F12 medium, IMDM medium and KnockOut™ DMEM medium (Life Technologies). Depending on the medium used, it may be necessary or desirable to add glutamine, vitamin C, one or more antibiotics such as streptomycin, penicillin and/or anti-mycotic such as Fungizone (amphotericin B).

According to a preferred embodiment, the medium comprises an algae growth factor as described above.

In more preferred embodiment, the medium does not comprise serum or serum albumin of animal origin. Said serum can be human patient or pooled human serum, fetal calf serum or bovine serum. Said albumin can be human serum albumin, bovine serum albumin.

Cells that can be cultured in using cell culture media of the present invention include stem cells, induced pluripotent stem cells, progenitor cells, and differentiated cells.

Examples of applications involving cell culture in which hydrogel of the invention can be used include, but are not limited to, proliferation of cells and tissues in vitro in an environment that more closely approximates that found in vivo (for example as research tools), screening of pharmaceutical compounds and toxicology assays in such cell cultures or tissues in vitro, cell therapy, cell delivery, drug delivery, biochemical replacement, production of biologically active molecules, tissue engineering (e.g., ex vivo organ model, tissue explants, in vivo tissue regeneration), biomaterial, and clinical trials.

The present following examples are not in any way limited to the embodiments described in this application and a person skilled in the art will be able to predict many possible changes to it without deviating from the main idea, as described in the claims.

Examples

1. Materials

Low-acyl gellan gum (Gelzan™ CM, G1910), magnesium chloride ($MgCl_2$, 208337), monosodium phosphate ($NaH_2PO_4$, S8282), sodium hydroxide (NaOH, S8045), sodium bicarbonate ($NaHCO_3$, S5761), potassium chloride (KCl, P9541), low-glucose (D5523) & high-glucose (D1152) Dulbecco's Modified Eagle's medium (DMEM), Accutase® solution (A6964), penicillin/streptomycin (P4333), paraformaldehyde (PFA, P6148) and tumor necrosis factor alpha (TNF-$\alpha$) were purchased from Sigma-Aldrich (St Louis, MO, USA). Sodium chloride (NaCl, 534900) was obtained from Unichem Ltd (Mumbai, Maharashtra, India), All salts were received in anhydrous form. Type-1 rat tail collagen (SC-136157) was procured from Santa Cruz Biotechnology, Inc. (Dallas, TX, USA). Fetal Bovine Serum (FBS) was obtained from Hyclone (South Logan, Utah, USA). Deionized water was the filtrate from Adrona Crystal multipurpose water purification system (Riga, Latvia). Ultra-pure grade phosphate-buffered saline (10×PBS) was procured from Vivantis Technologies Sdn Bhd (Subang Jaya, Selangor Darul Ehsan, Malaysia). 0.22 μm filter units were obtained from Sartorius AG (Göttingen, Germany). CellTiter 96® AQueous One Solution Cell Proliferation Assay (MTS) was purchased from Promega (Madison, WI, USA). Triton-X was obtained from Bio-Rad Laboratories (Hercules, CA, USA). Phalloidin-iFluor 488 Reagent (ab176753) was acquired from Abcam (Cambridge, UK). 4-well chamber slides and their respective chamber glass covers were purchased from Thermo Fisher Scientific (Waltham, MA, USA). TSG-6 ELISA kit was obtained from RayBiotech (Peachtree Corners, GA., USA).

Human Dermal Fibroblast (HDF), human Mesenchymal Stem Cells (hMSC, PT-2501) and Adipose-derived Stem Cells (ADSC, PT-5006) were purchased from Lonza Bioscience (Singapore). All stem cell donors were tested negative for mycoplasma, bacteria, yeast, and fungi. HIV-1, hepatitis B and hepatitis C. hMSC are guaranteed through 5 passages, to express CD29, CD44, CD73, CD90, CD105, and CD166 and to not express CD14, CD19, CD34, and CD45. ADSC are guaranteed through 5 passages, to express CD13, CD29, CD44, CD73, CD90, CD105, and CD166 and to not express CD14, CD31, and CD45.

2. Preparation of the Gellan Gum Hydrogel

Gellan gum solution is prepared by dissolving dry gellan gum (Gelzan™ CM, G1910, Sigma-Aldrich) at a concentration of 0.762% (w/v) in water. 3154, of the gellan gum solution is incubating at 90° C. for 30 minutes on a dry hot bath. The gellan gum solution is then incubating at 37° C. for at least 15 minutes on a dry hot bath.

Neutralized 3.33 mg/mL type-1 collagen (sc-136157, Santa Cruz Biotechnology, Inc) is freshly prepared. 1804, of collagen solution is transferred to the 315 μL of gellan gum solution.

When gellan gum is crosslinked before collagen (Full simultaneous IPN (crosslink gellan gum first)), the ionic crosslinking agent $MgCl_2$ is added to the mixture at room temperature and finally the mixture is heated at 37° C. for 30 min for collagen fibrillogenesis.

When collagen is crosslinked before gellan gum (Full simultaneous IPN (collagen crosslink first)), the mixture is incubated for 20 to 30 minutes at 37° c. Ionic crosslinking agent solution is prepared with 0.114% (w/v) of $MgCl_2$ before to be transferred in gellan gum-collagen solution and the solution is stand for 5 minutes at room temperature.

The final concentration of gellan gum, $MgCl_2$ and collagen are 0.4% (w/v), 0.02% (w/v) and 1 mg/mL respectively.

3. Gelation of the Gellan Gum Hydrogel

3.1 Rheometry Method

Rheological characterization of the hydrogels was performed with an oscillatory rheometer (MCR 302, Antor Paar, Austria), using plate-plate geometry (diameter=8 mm, working gap=1 mm). 100 μL of freshly prepared hydrogels were quickly transferred onto the base plate of the rheometer prior to each testing. Tests were performed using three different samples per hydrogel composition. After lowering the upper cone plate to a gap of 1 mm with the base plate, hydrogel sample was allowed to stabilize for 1 minute. All measurements were conducted at 25° C.

Amplitude sweeps were always first conducted to determine the limit of the linear viscoelastic region (LVR). The limit is a percentage shear strain below which frequency sweeps can be carried out without deforming the samples. Storage (G') and loss (G") moduli were obtained between the ranges of 0.1 to 100% shear strain at a constant frequency of 1 Hz. The linearity limit was determined using a ruler on the graph plotted.

The shear-dependent behavior and inner structure of hydrogels were studied via frequency sweeps. G' and G" moduli measurements were completed from minimum to maximum frequency between 0.1 to 100 rad/s. Shear strain was set to a constant, below the predetermined LVR prior to initiation of each measurement.

To understand the temperature- and time-dependent gelation behavior of IPN hydrogels, constant dynamic mechanical rheometry were carried out. Both temperature and time sweeps were conducted at a constant 1% shear strain and a constant frequency of 1 Hz. For temperature sweeps, measurements at $-2°$ $C.^{-1}$ from 50 to 10° C. were conducted. While for time sweeps, hydrogel sample was not allowed time for equilibration and G'/G" measurements were taken every 5 seconds up to 2 minutes.

The results of the rheological sweeps were presented in a diagram with the G' and G" plotted on the y-axis and the respective parameters plotted on the x-axis, with both axes on a logarithmic scale.

3.2 Gel Yield Method

For gel yield, 600 μL of hydrogels (n=3) were blot-dried and weighed before lyophilization ($W_i$). Lyophilized hydrogels were soaked in 600 μL of deionized water at 37° C. with constant agitation of 60 rpm for 3 days. The reconstituted wet hydrogels were then blot-dried and re-weighed ($W_r$). The percentage gel yield was determined according to the following equation:

$$\text{Gel yield} = \left(\frac{Wr}{Wi}\right) \times 100\% - (3)$$

3.3 Results

Cell behaviour is largely influenced by the stiffness of the hydrogel scaffolds (Bischofs, I. B. and U.S. Schwarz. PNAS, 2003, 100(16):9274-9279; Fratzl, P. and F. G. Barth. Nature, 2009, 462(7272): p. 442; Ahearne, M. Interface focus, 2014, 4(2): p. 20130038). The higher the G' (storage modulus), the stiffer the material. Enger et al. suggested that softer materials with storage moduli less than 3,000 Pa do not induce spontaneous differentiation (Engler, A. J., et al. Cell, 2006. 126(4): p. 677-689). On the other hand, a softer gel may not establish a cellular context to promote cell adhesion (Discher, D. E et al. Science, 2005. 310(5751):1139-1143), only stiffer hydrogels with storage moduli above 2,000 to 3,000 Pa facilitated cell adhesion and spread (Yeung, T., et al. Cell motility and the cytoskeleton, 2005. 60(1):24-34). Also, a previous study showed that incorporation of gelatin (chemical derivative of collagen) into an existing hydrogel network increased its storage moduli by 2.4- to 3.4-fold (Miao, Tet al. Journal of Materials Chemistry B 2015, 3 (48), 9242-9249). Therefore, to ensure the resultant interpenetrating polymer network (IPN) hydrogel's storage modulus fall within the optimal range for cell spread and nonspontaneous differentiation, the concentration of 0.4% (w/v) gellan gum and 0.02% (w/v) $MgCl_2$ were selected (Table 1).

TABLE 1

| Concentration of Gellan Gum (w/v) | Concentration of $MgCl_2$ (w/v) | LVR[a)] | G' at 1 Hz (Pa)[b)] |
|---|---|---|---|
| 0.3% | 0.01% | =1% | 144.1 ± 5.17 |
| | 0.02% | =1% | 394.6 ± 49.7 |
| | 0.03% | =0.5% | 760.5 ± 44.4 |
| 0.4% | 0.01% | =0.5% | 146.0 ± 8.07 |
| | 0.02% | =1.5% | 621.1 ± 83.4 |
| | 0.03% | =0.5% | 1033.2 ± 142.2 |
| 0.5% | 0.01% | =1% | 158.1 ± 3.62 |
| | 0.02% | =1% | 1230.6 ± 194.8 |
| | 0.03% | =0.5% | 1380.0 ± 146.6 |

[a)]Linear Viscoelastic Range (LVR) was determined from an amplitude sweep of the hydrogel sample at constant frequency of 1 Hz at 25° C. Percentage shear strain values were reported.

[b)]Storage modulus (G') was determined from an oscillatory frequency sweep of the hydrogel sample, at the upper limit of the LVR and 25° C. Values at 1 Hz are reported. Results are presented as mean (n = 3) ± SD.

Figure 1:
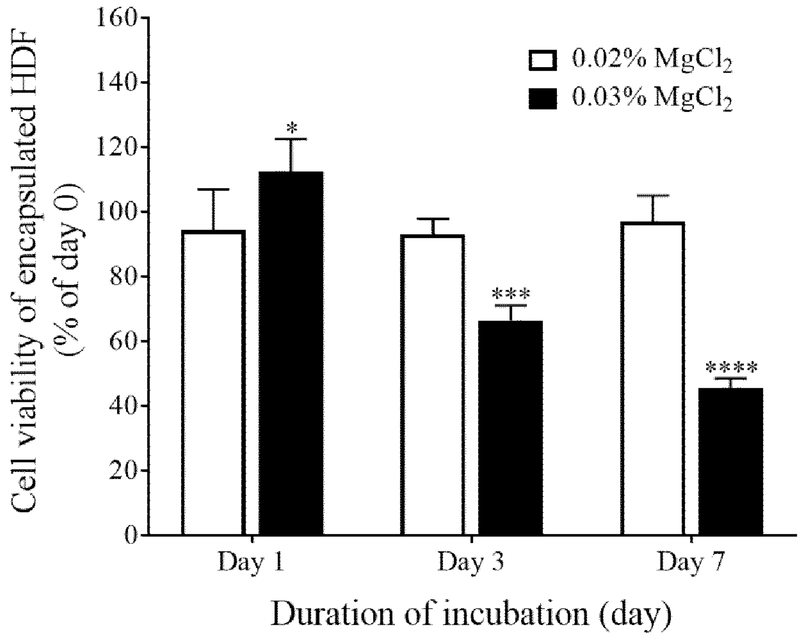
FIG. 1. Cell viability of HDF encapsulated within gellan gum hydrogels formed with 0.4% gellan gum and 0.02% or 0.03% MgCl2. The mean (n=3) and SD are shown.

The combination of 0.4% (w/v) gellan gum and 0.03% (w/v) $MgCl_2$ was not selected due to potential cell toxicity issue (FIG. 1).

The most commonly applied technique to form an IPN is by an in-situ preparation where the polymers are mixed in a solution before simultaneous, yet orthogonal crosslinking is carried out. However, the mixing of collagen with gellan gum could reduce the proximity of the carboxylate groups on gellan gum for ionic crosslinking. The semi-IPN comprising of 2 mg/mL collagen did not form (Table 2). To overcome this issue, the inventors proposed reducing the concentration of collagen. A weak hydrogel was formed when collagen concentration was reduced to 1 mg/mL.

Next, the inventors sought to form a full IPN hydrogel to reduce the rapid seepage of collagen from the gellan gum hydrogel network. Attempts were unsuccessful if gellan gum was crosslinked before collagen. When the order was reversed, a full simultaneous IPN hydrogel with an average storage modulus of 2353.9±110.2 Pa was successfully fabricated. This IPN hydrogen was subsequently used in the following experiments.

TABLE 2

Optimization of the gelation protocol of IPN hydrogels based on feasibility of gelation and resultant hydrogel rheological properties.

| Type of Hydrogel[a] | Concentration of Gellan Gum (w/v) | Concentration of $MgCl_2$ (w/v) | Concentration of Collagen (mg/mL) | G' at 1 Hz (Pa)[b] |
|---|---|---|---|---|
| Pure Collagen | — | — | 3.333 | 143.2 ± 10.3 |
| Pure Gellan gum | 0.4% | 0.02% | — | 621.1 ± 83.4 |
| Semi Simultaneous IPN (did not crosslink collagen) | 0.4% | 0.02% | 2 | Gelation did not occur; gel fragmentation indicating phase separation |
| Semi Simultaneous IPN (did not crosslink collagen) | 0.4% | 0.02% | 1 | 1303.9 ± 144.6 |
| Full Simultaneous IPN (crosslink gellan gum first) | 0.4% | 0.02% | 1 | Gelation did not occur |
| Full Simultaneous IPN (crosslink collagen first) | 0.4% | 0.02% | 1 | 2353.9 ± 110.2 |

The rheological properties of gellan gum-collagen IPN hydrogels with an average storage modulus of 2353.9±110.2 Pa are indicated in the table 3 below.

TABLE 3

Composition and rheological properties of gellan gum-collagen IPN hydrogels.

| Amount of Gellan Gum | Amount of Crosslinker | Bioactive Component | LVR[a] | G' at 1 Hz (Pa)[b] | Gelation Temperature[c] | Gelation Time[d] |
|---|---|---|---|---|---|---|
| 0.4% w/v | 0.02% $MgCl_2$ | 1 mg/mL rat-tail type-1 collagen | 1.1% | 2353.9 ± 110.2 | 36° C. | Instant (<5 s) |

[a]Linear Viscoelastic Range (LVR) was determined from an amplitude sweep of the hydrogel sample at constant frequency of 1 Hz at 25° C. Percentage shear strain values were reported.
[b]Storage modulus (G') was determined from oscillatory frequency sweep of the hydrogel sample at frequency of 1 Hz, at the upper limit of the LVR at 25° C.
[c]Gelation temperature was determined from the temperature sweep of the hydrogel sample at constant shear strain of 1% and constant frequency of 1 Hz at 25° C. Measurements were conducted at −2° C. per measurement from 50 to 10° C.
[d]Gelation time was determined from time sweep of the hydrogel sample at constant shear strain of 1% and constant frequency of 1 Hz at 25° C. Continuous measurements were done at the interval of 5 s up to a total of 120 s.

Therefore, the storage modulus of 2353.9±110.2 Pa is a good fit for mesenchymal stem cells.

The results obtained for both temperature and time of gelation provide important information concerning subsequent clinical applications. Temperature on the skin surface is 34° C. As gellan gum exhibits cold gelation mechanism, IPN hydrogel could form directly on the skin upon addition of the crosslinker. The quick gelling time may be useful in the use of IPN hydrogel in an injectable system.

Gel yield reflects the robustness of a hydrogel's network. A higher gel yield indicates that the hydrogel is able to expand and contract in response to absorption and evaporation of its water content. The incorporation of collagen increased the gel yield of gellan gum hydrogels from 85.9±5.2% to 95.8±1.52% (Table 4).

TABLE 4

Composition, gelation time and gel yield of IPN and pure gellan gum hydrogels.

| Amount of Gellan Gum | Gellan Gum Crosslinker | Secondary component | Gelation Time | G' at 1 Hz (Pa) | Gel Yield (%)[a] |
|---|---|---|---|---|---|
| 0.4% w/v | 0.02% $MgCl_2$ | 1 mg/mL rat-tail type-1 collagen | Instant (n = 3) | 2353.9 ± 63.6 | 95.8 ± 1.52 |
| 0.4% w/v | 0.02% $MgCl_2$ | — | Instant (n = 3) | 621.1 ± 48.1 | 85.9 ± 5.2 |

[a]Gel yield was expressed as $[(W_2 \div W_1) \times 100]$% whereby, $W_1$ = wet weight of hydrogel before freeze drying (lyophilization) and $W_2$ = wet weight of hydrogel reconstituted after freeze drying.

3.4 Scanning Electron Microscopy

3.4.1 Method

Lyophilized hydrogel samples were first frozen in liquid nitrogen before being separated at their cross-sections. Then, the dissected hydrogels were quickly mounted onto pin stubs with their cross sections facing the electron emission source. The samples were subsequently sputter coated with gold and examined with JEOL JSM 6510 scanning electron microscope (JEOL Ltd, Akishima, Tokyo, Japan). Largest pore sizes were calculated with reference to an in-built scale bar. At least 3 different locations of the cross-sections for each specimen were imaged. The process was repeated at 3 different optical zooms.

3.4.2 Results

Figure 2:
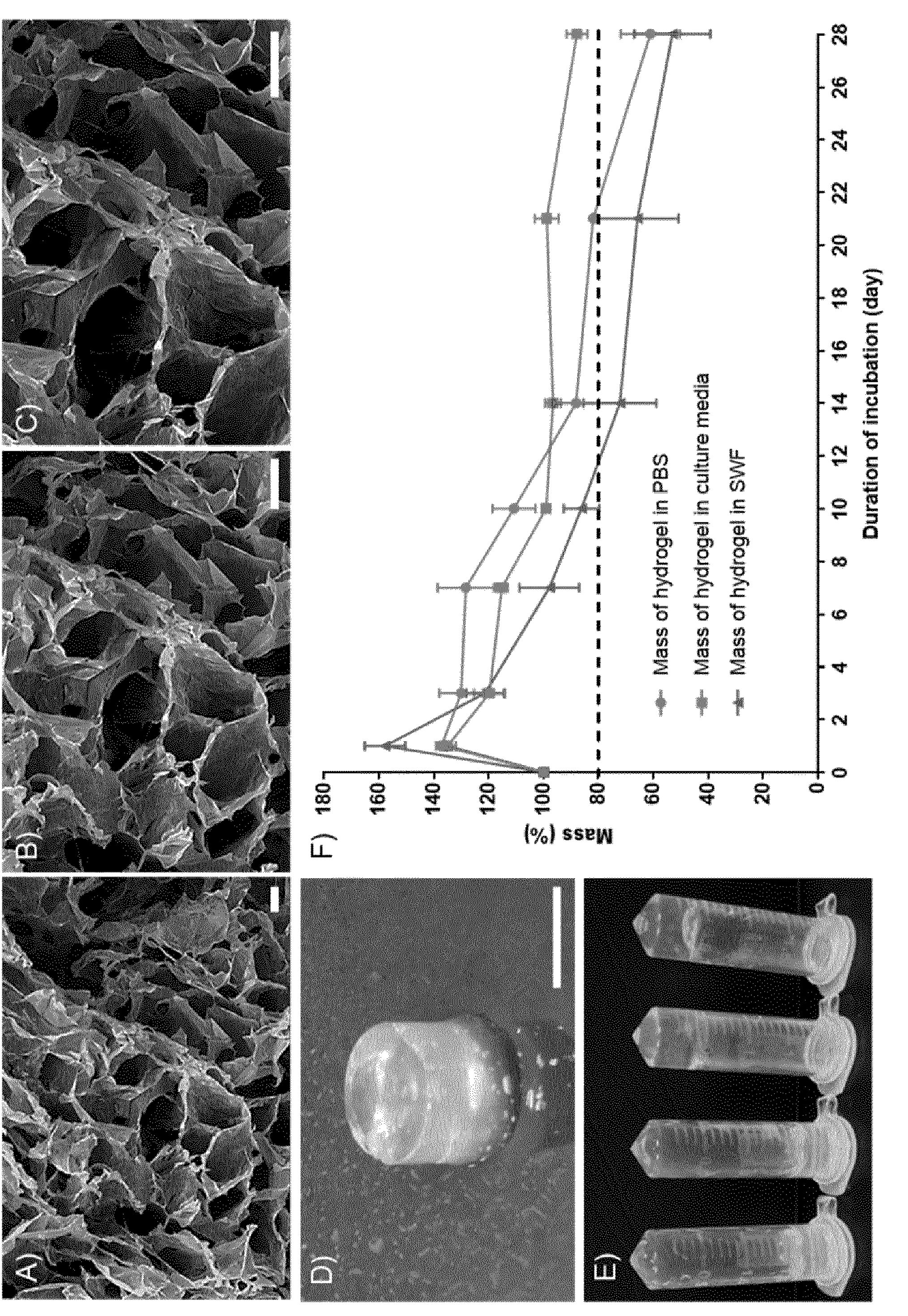
FIG. 2: Physical characteristics of gellan gum-collagen interpenetrating polymer network (IPN) hydrogels. SEM of the cross-section of the IPN hydrogel at A) 100×, B) 150× and C) 200× zoom (scale bar: 100 μm). D) Image of IPN hydrogel conforming to a cylindrical shape (scale bar: 1 cm). E) (from left to right) 0.4% gellan gum, 0.4% gellan gum & 1 mg/mL collagen mixture, 0.4% gellan gum & 1 mg/mL collagen mixture heated at 37° C. for 30 minutes and 0.4% gellan gum & 1 mg/mL collagen mixture heated at 37° C. for 30 minutes then crosslinked with 0.02% $MgCl_2$. F) Degradation (weight loss) of IPN hydrogel over the duration of 28 days. The mean (n=3) and standard error of mean (SEM) are shown. All samples were soaked in respective solutions and incubated at 37° C. with mild agitation at 60 rpm.

The porous structure of the IPN hydrogel will allow the transport of nutrients, metabolites, and other important regulatory molecules between the encapsulated cells and extracellular media (FIG. 2A-C).

3.5 In Vitro Hydrogel Degradation Study

3.5.1 Methods

Simulated Wound Fluid (SWF) was prepared when 0.35 g $NaH_2PO_4$, 0.68 g NaCl, 2.5 g $NaHCO_3$ and 0.22 g KCl were dissolved in 100 mL of deionized water (pH=8.00±0.05).

For the in vitro degradation study, 600 μL of hydrogels were formed in 2 mL Eppendorf tubes before being blot-dried and transferred into 15 mL Falcon tubes (n=3). Each Falcon tube was weighed before and after the transfer to determine the hydrogel's initial weights (Wi). The hydrogels were immersed and incubated in 2 mL of 1×PBS, culture media or SWF at 37° C. under constant agitation of 60 rpm, for a total of 28 days. At day 1, 3, 7, 10, 14 and 28, Falcon tubes were centrifuged at 4000 rpm for 2 minutes, the supernatant was decanted, and the remaining hydrogels were blot-dried and weighed ($W_d$). Difference in mass of the wet hydrogels was calculated at each time-point against that of day 0's by the following equation (Equation (1)). 2 mL of fresh 1×PBS, culture media or SWF was replenished after each time-point until the 28$^{th}$ day of incubation.

$$\% \text{ Mass change} = (W_d/W_i) \times 100 \quad (1)$$

$W_i$—Initial wet hydrogel weight $W_d$—Wet hydrogel weight at each time-point

3.5.2 Results

The qualitative inversion test showed that gellan gum and gellan gum-collagen are clear, free-flowing solutions. A solid mass capable of holding its own weight was formed when the gellan gum-collagen mixture was heated at 37° C. for 30 minutes. The same solid mass retained upon subsequent crosslinking with $MgCl_2$. Gelation of the IPN hydrogels was shown qualitatively when the clear content did not flow upon inversion of the Eppendorf tube (FIG. 2D-E).

Weight loss over time was used as a measure of hydrogel degradation. For physically crosslinked hydrogels, degradation is observed due to the gradual disruption of cross-linkage through ion-exchange mechanism. Free polymeric materials then diffuse into the solvent resulting in a decrease in gel mass. More than 80% of the IPN hydrogels remained after 12 days of incubation with SWF (FIG. 2F). Therefore, they are likely able to retain structural integrity on wound beds for at least a week.

4. In Vitro Characterization: Cell Attachment of Encapsulated Cells

4.1 Method for Assessment of Cell Attachment of Encapsulated Cells

For morphological studies, 200 μL of hydrogel containing 1000 cells/μL was added into each well of 8-chamber (HDF) and 4-chamber glass slide (stem cells) (n=2). 400 μL of media was added to each HDF-laden hydrogel while 800 μL of media was added to each stem cell-laden hydrogel. The cells were stained and imaged on the same day (day 0). To visualize cells incubated for different durations, they were seeded in a countdown fashion.

Cells were stained according to the manufacturer's protocol. Briefly, cell culture media were carefully aspirated to avoid dislodging any hydrogel. Each hydrogel was rinsed once with 1×PBS to remove phenol red. To fix the encapsulated cells, cell-laden hydrogels were incubated with 200 μL (HDF) or 500 μL (stem cells) of 4% formaldehyde in PBS for 30 minutes. After which, cells were incubated with the same volumes of 0.1% (v/v) Triton X-100 for 5 minutes to increase cell permeability. The permeabilized cells were then incubated with 1× Phalloidin conjugate working solution for 90 minutes in the dark. Subsequently, all stained cells were thoroughly washed three times with 1×PBS to remove excess phalloidin conjugate, a critical step to avoid leaving entrapped residuals within the hydrogel network.

Confocal z-stack images were captured with Olympus FluoView FV1000 (Olympus, Japan) confocal laser scanning microscope (CLSM) using a 20×/1.45 oil objective, with 543 nm HeNe laser as the excitation source. Image was stitched with Tile Scan mode of 4 by 3 frames. The images were digitally stacked by Imaris 9.1.3 (Belfast, UK) to produce 3D images of encapsulated cells in hydrogels.

4.2 Results

High density fibroblast (HDF) cultured on the gellan gum hydrogel without collagen (lower panel) do not spread and propagate significantly from day 0 to day 7. On the contrary, HDF cultured on the gellan gum hydrogel comprising collagen can spread and propagate (indicated by increase in cell density).

Figure 3A:
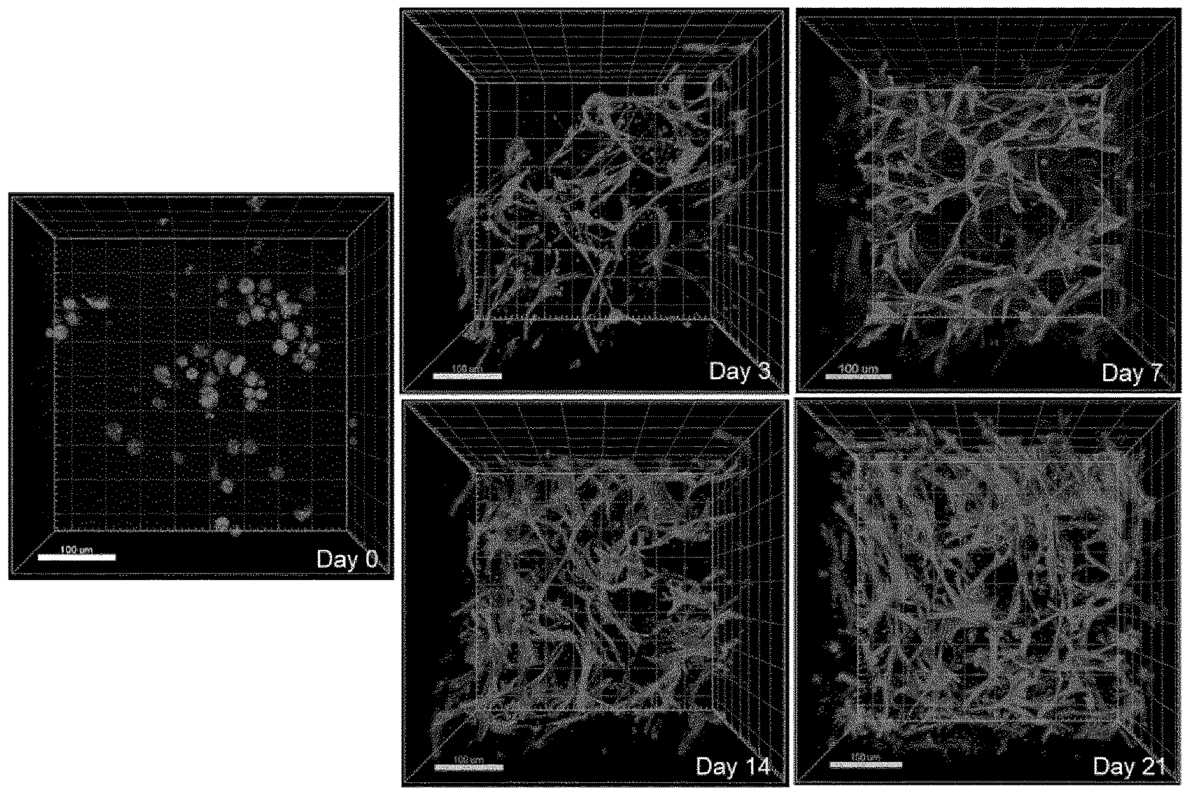
Figure 3B:
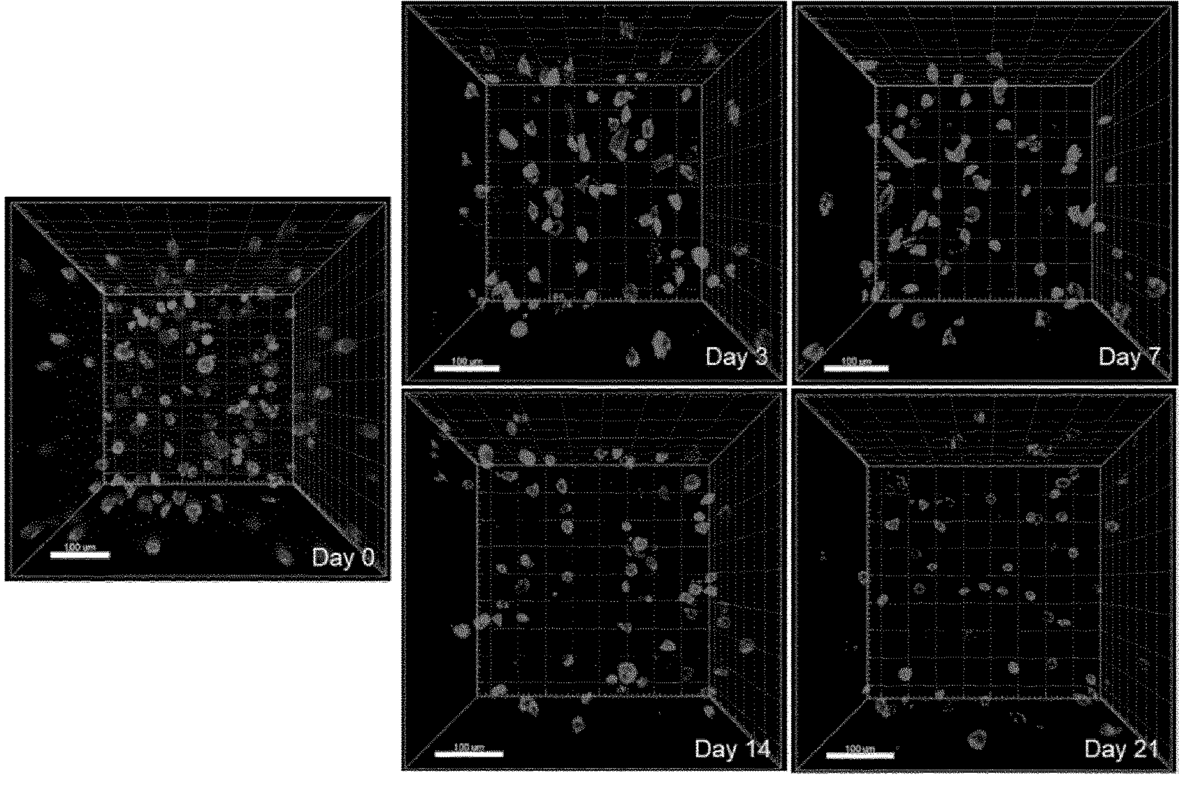

3D confocal images allowed observation of how the encapsulated cells spread within the hydrogels. Mesenchymal stem cells began to spread and form cellular protrusions into the IPN hydrogel matrices (FIG. 3A). Whereas, cells encapsulated in pure gellan gum hydrogels remained in their rounded morphology throughout the duration of incubation (FIG. 3B). This proved that the presence of the collagen network allowed adherent cells such as MSC to attach and spread. Cell adhesion to matrix is critical for cellular homeostasis of adherent cells. They begin to undergo a programmed cell death called anoikis in the absence of adhesion substrates.

5. In Vitro Characterization: Cell Proliferation of Encapsulated Cells

5.1 Method for Assessment of Cell Proliferation of Encapsulated Cells

To determine the cell viability of mammalian cell lines encapsulated within the hydrogels, MTS (3-(4,5-dimethylthiazol-2-yl)-5(3-carboxymethoxyphenyl)-2(4-sulfofenyl)-2H-tetrazolium) assays were conducted. Viable and hence, metabolically active cells are able to convert MTS into a brown formazan product by their mitochondrial dehydrogenase enzyme.

Briefly, 10 μL of MTS was added per 100 μL of culture media at different time-points after cell encapsulation (n=3). For HDF and Adipose-derived stem cells (ADSC), MTS was added on day 0 (6 hours after encapsulation), 1, 3 or day 7, for MSC, MTS was added on day 0, 1, 3, 7, 14 or day 21. Cells were further incubated for 3 h at 37° C. in a humidified atmosphere of 5% $CO_2$ in air. After incubation, 100 μL of the supernatant of each well was transferred to a new well in a clear, round, flat-bottom 96-well plate.

The measurement of total metabolic activity, which is linearly proportional to the number of viable cells, was done on a multi-well microplate reader (Hidex Sense, Turku, Finland) at $OD_{490}$. Cell-free hydrogels treated in the same way were used as "blanks". Cell proliferation was determined by expressing the blank-corrected $OD_{490}$ values on day 1, 3 and 7 against that of day 0's. For stem cells (hMSC and ADSC), the whole experiment was repeated (n=3) with time points at day 0, 1, 3, 7, 14 and 21.

5.2 Results

As shown in the FIG. 4, cell growth was inhibited when HDF were encapsulated in pure gellan gum hydrogels (full serum), but no cell death was observed. CGF did improve cell viability but did not significantly improve it.

Cell death was observed when serum-free media was given to HDF, ADSC or MSCencapsulated in pure gellan gum hydrogels (FIGS. 4 and 5). CGF did slow down the death rate. Cell death was also observed when serum-free media was given to HDF encapsulated in IPN hydrogels. However, the presence of CGF revitalized the cells, maintaining growth throughout. When HDF is cultured on the gellan gum hydrogel comprising collagen and forming the interpenetrating network, with CGF replacing serum, cell growth is sustained throughout 7 days.

The presence of serum has masked the proliferative effect of CGF on encapsulated ADSC. Cell viability of ADSC was not significantly increased in the presence of 10% (v/v) FBS (FIG. 6). Also, in the absence of serum, encapsulated stem cells rapidly perished and cell viabilities continued to decrease below 10% after 3 weeks of culture. The presence of 1 g/L CGF slowed down the death rate but, did not reverse the course of action.

By removing half of the serum in culture media, encapsulated ADSC quickly perished, cell viability is of 30.4±4.68% after 21 days of culture. Strikingly, 1 g/L CGF preserved the viability of encapsulated ADSC in such conditions. When the serum-reduced media was supplemented with 1 g/L CGF, cell viability reached 124.0±7.57%, indicating cell proliferation.

6. Scratch Assay

6.1 Method for Scratch Assay

To assess if ADSC encapsulated within IPN hydrogel could secrete paracrine wound healing factors upon exposure to inflammatory cytokines like TNF-α, in vitro 2D scratch assays were performed. First, ADSC-equilibrated media were prepared by incubating 600 μL of IPN hydrogel containing $6\times10^5$ of encapsulated ADSC, for 72 hours in 2 mL of serum-free DMEM. A total of 10 mL of ADSC-equilibrated media were collected from 5 separate wells of a clear, round, flat-bottom 6-well plate. Gel-equilibrated media were prepared in the same manner using cell-free IPN hydrogels. After the media were collected, they were centrifuged at 1500 rpm for 10 minutes, and the supernatant were stored at −80° C. until further use. Non-equilibrated culture media supplemented with FBS was used as positive controls (normal media) and non-equilibrated culture media without FBS was used as negative controls (serum-free media). All culture media contains 10 ng/mL of TNF-α to induce secretion of TSG-6.

The scratch assays were conducted using CytoSelect™ 24-well Wound Healing Assay Kit (Cell Biolabs Inc., San Diego, CA, USA), according to the manufacturer's protocol. Briefly, 500 μL of HDF suspension at $5\times10^5$ cells/mL of normal media were added to each well of a 24-well plate. Plastic inserts were placed to ensure consistent wound field ("wounded" area) with a defined 0.9 mm gap was created in each well. The cells were incubated at 37° C. in a humidified atmosphere of 5% $CO_2$ in air until a monolayer formed.

After which, the plastic inserts were carefully removed, and the cells were rinsed three times with sterile 1×PBS. Immediately after rinsing, 500 μL of ADSC-equilibrated, gel-equilibrated, normal or serum free media were added to designated wells (n=3). The differential rates of wound closure were monitored with a light microscope (Olympus CKX41, Shinjuku, Tokyo, Japan). Images of the wound gaps were captured at different time-points of 0 ($L_i$), 6, 12, 24 and 48 hours. Migration rate was determined by following the equation:

$$\%\ \text{Wound closure}=(L_i-Lc)/L_i\times100;$$

$L_i$ represents the initial length of wound gap $L_c$ represents the length of wound gap at each time-point

6.2 Results

Figure 7A:
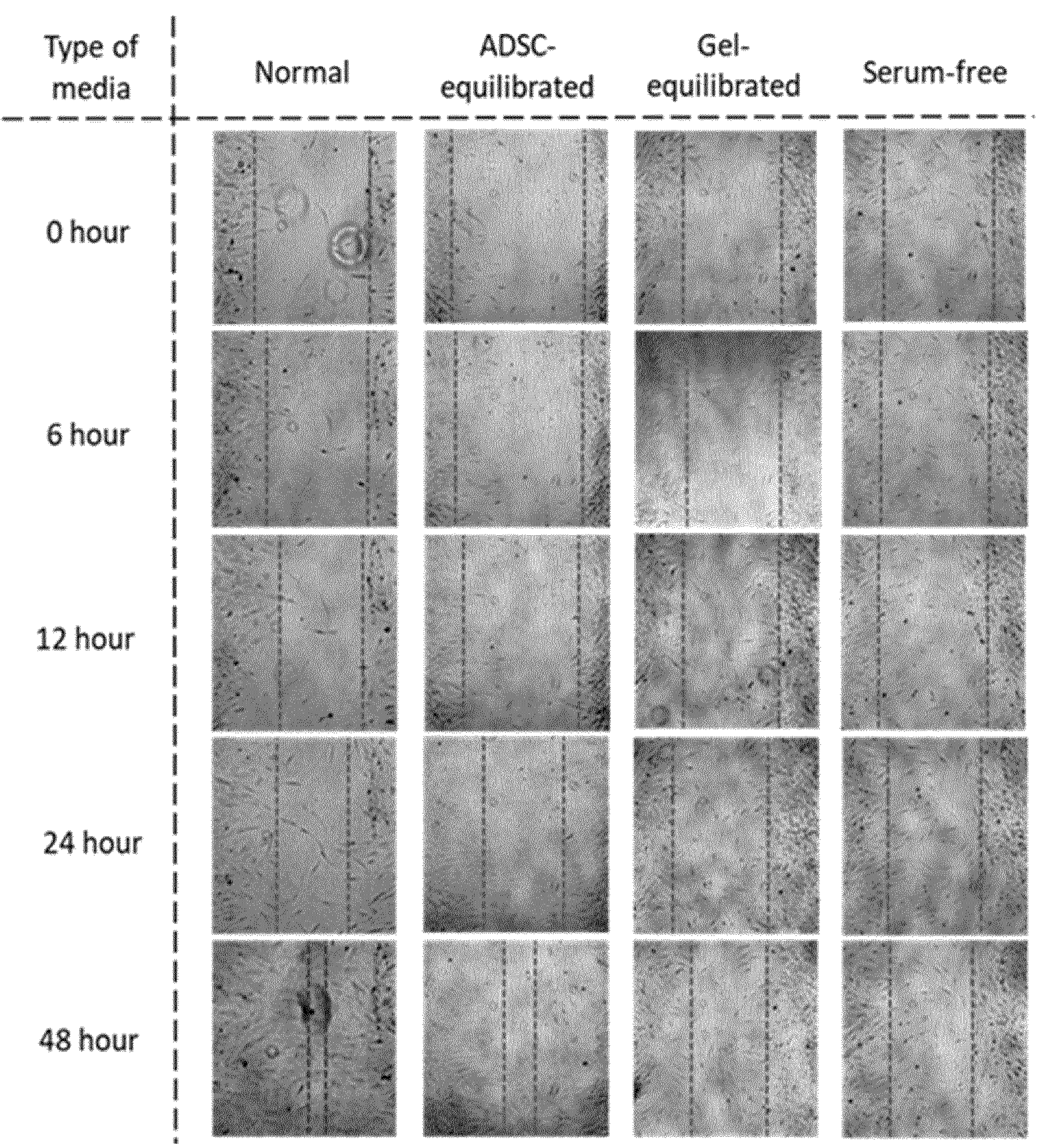
Figure 7B:
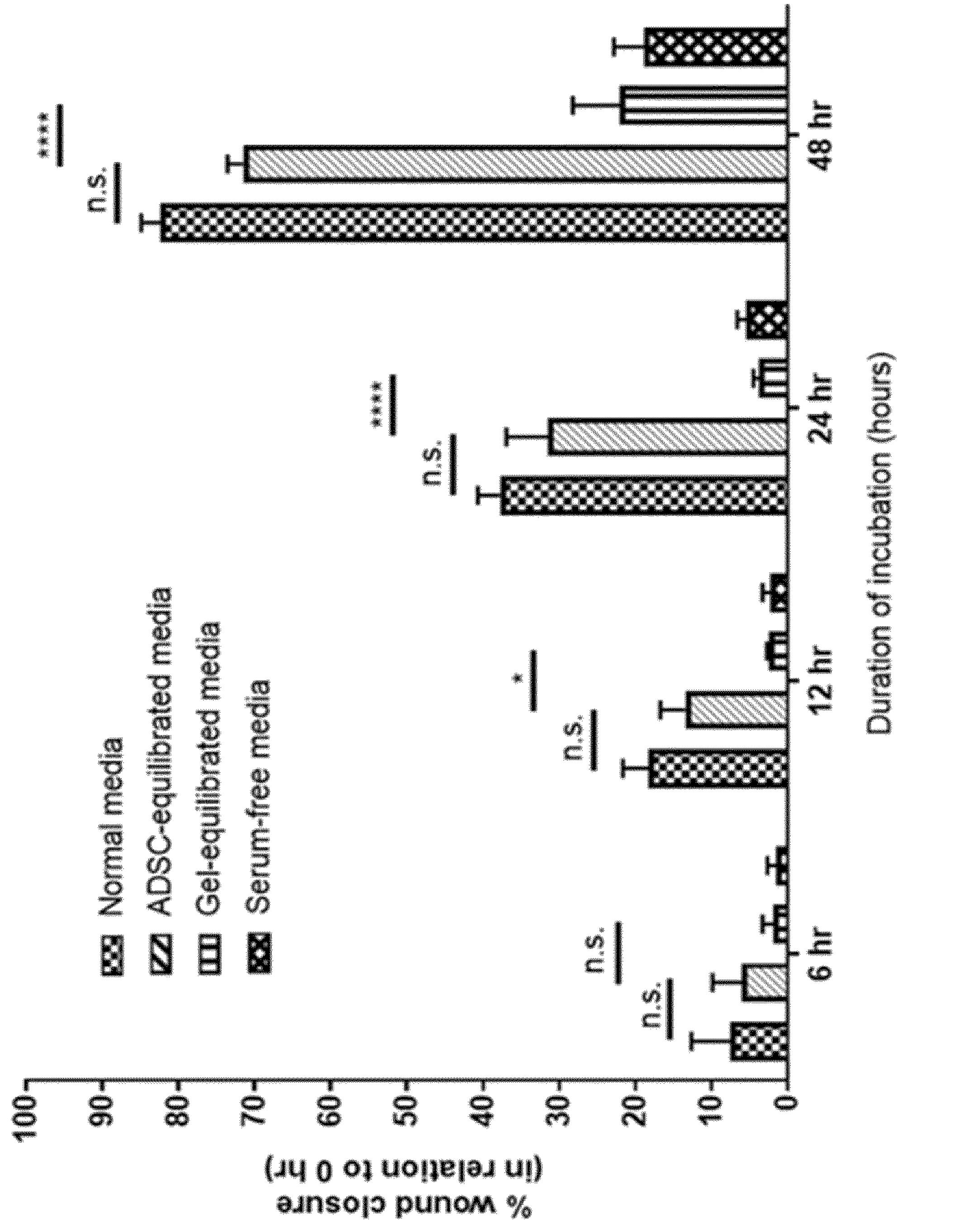

In response to biochemical precursors found in serum, HDF migrated and covered up to 82.4±2.57% of the "wounded area" after 48 h of incubation. Whereas, the lack of serum supplementation prevented the migration of HDF significantly, achieving a percentage wound closure of only 18.9±3.93%. On contrary, the ADSC-equilibrated serum-free media appeared to provide chemotactic stimuli to HDF, promoting "wound closure" as far as 71.5±2.08% over the duration of the experiment (FIG. 7A-B). The cell-free IPN hydrogels did not provide any substrates that could promote cell growth or migration. Percentage wound closure for HDF exposed to gel-equilibrated media only managed 22.1±6.21% after 48 h of incubation. These results suggested that ADSC encapsulated within IPN hydrogels secreted bioactive factors which induced significant HDF growth and migration. This could be correlated to enhance wound closure rate in physiological wound healing process.

7. ELISA Assay for Human TSG-6

7.1 Methods

The quantification of anti-inflammatory TSG-6 protein released from ADSC-laden IPN hydrogels (n=5) upon stimulation with TNF-α was examined with ELISA test kit from RayBiotech (Peachtree Corners, GA, USA) using the manufacturer's protocol.

ADSC-conditioned media were prepared by incubating 600 μL of IPN hydrogel containing $6\times10^5$ of encapsulated ADSC, for 72 hours in 2 mL of serum-free DMEM. A total of 10 mL of ADSC-conditioned media were collected from 5 separate wells of a clear, round, flat-bottom 6-well plate. Gel-conditioned media were prepared in the same manner using cell-free IPN hydrogels. After the media were collected, they were centrifuged at 1500 rpm for 10 minutes, and the supernatant were stored at −80° C. until further use. Non-conditioned culture media supplemented with FBS was used as positive controls (normal media) and non-conditioned culture media without FBS was used as negative controls (serum-free media). All culture media contains 10 ng/mL of TNF-α to induce secretion of TSG-6 from encapsulated ADSC.

7.2 Results

TSG-6 is a powerful anti-inflammatory paracrine secreted by ADSC. The detection of human TSG-6 from human ADSC encapsulated within the IPN hydrogels indicates that the overall biologic wound dressing construct could release anti-inflammatory paracrine and exhibit potential anti-inflammatory paracrine activity upon application and subsequent exposure to the wound cytokine, TNF-alpha, on burn wounds.

8. In Vivo Full-Thickness Burn Wound Creation Procedure (FIG. 9)

Inhalational induction anaesthesia was achieved with 5% Isoflurane (Attane™, JD Medical, USA) and maintained at 1.5% Isoflurane. Hair on the lower right posterior dorsum area of mice were cleanly removed using Veet™ hair removal cream (Reckitt Benckiser Group, UK). Full thickness burn injuries were generated. Pre-operative subcutaneous (SC) Buprenorphine (0.1 mg/Kg BW) was given 30 min prior to burn wound creation. Next, a stainless-steel bar (96.2 g) was heated in a 100° C. water bath for 15 min before its template hot surface of 6 mm×5 mm was placed on the shaven posterior-dorsum of each mouse for 30 seconds. Post-operative SC buprenorphine was given 8-hourly for 48 hours. After which, the burn wounds were excised by removing the eschar, the wounds were then treated with 60 μL of hydrogels. All wounds, including controls, were covered with a secondary Tegaderm wound dressing. Analgesic SC buprenorphine was given 12-hourly until further assessment by a veterinary surgeon. Mice were housed individually in environmentally enriched cages throughout the experiment. They were euthanized by CO2 inhalation followed by cervical dislocation at the referred time points.

The invention claimed is:

1. A hydrogel comprising a gellan gum polymer network and collagen for use in the wound treatment in a subject in need thereof, wherein said hydrogel comprises a full interpenetrating polymer network comprising:

a thermally crosslinked collagen, and a ionically crosslinked gellan gum, wherein the hydrogel comprises from 0.2% (w/v) to 1% (w/v) gellan gum and from 0.1% (w/y) to 0.2% (w/v) of collagen, and wherein the full interpenetrating polymer network is obtained by ionically crosslinking the gellan gum using a divalent cation as ionic cross-linking agent, in the presence of the thermally crosslinked collagen, using $Mg^{2+}$ as the ionic cross-linking agent, wherein the interpenetrating polymer network comprises from 0.01% (w/v) to 0.03% (w/v) $Mg^{2+}$, and wherein the hydrogel has a storage modulus (G') of 2000 to 3000 Pa, as measured at 1 Hz at 25° C.

2. The hydrogel for use of claim 1 comprising about 0.1% (w/v) of collagen.

3. The hydrogel for use of claim 1 comprising about 0.4% (w/v) of gellan gum.

4. The hydrogel for use of claim 1 comprising about 0.02% (w/v) of $Mg^{2+}$.

5. The hydrogel for use according to claim 1 wherein said hydrogel further comprises an algae growth factor.

6. The hydrogel for use of claim 5 wherein said algae growth factor is a *chlorella* growth factor.

7. The hydrogel for use of claim 6 comprising between 0.1 and 1% (w/v) of *chlorella* growth factor.

8. A wound dressing comprising the hydrogel according to claim 1.

9. A wound dressing comprising a hydrogel according to claim 1 and algae growth factor, preferably *chlorella* growth factor.

10. A wound dressing of claim 8 further comprising a pharmaceutically acceptable carrier.

11. A wound dressing according to claim 8 for use in the wound treatment in a subject in need thereof.

12. A cell culture system comprising a hydrogel according to claim 1 and a cell culture medium comprising an algae growth factor.

13. The cell culture system of claim 12 wherein said cell culture medium is free of serum or albumin.

14. The hydrogel of claim 1, wherein the hydrogel has a storage modulus (G') of 2000 to 2500 Pa, as measured at 1 Hz at 25° C.

15. The hydrogel of claim 1, wherein said hydrogel comprises a full interpenetrating polymer network comprising:—about 0.4% (w/v) gellan gum, about 0.1% (w/v) of collagen, and about 0.02% (w/v) of $Mg^{2+}$.

* * * * *